United States Patent [19]

Hamill et al.

[11] Patent Number: 4,683,201
[45] Date of Patent: Jul. 28, 1987

[54] ANTIBIOTIC A80190-PRODUCING ACTINOMADURA OLIGOSPORA AND PROCESS

[75] Inventors: Robert L. Hamill, Greenwood; Raymond C. Yao, Carmel, both of Ind.

[73] Assignee: Eli Lilly and Company, Indianapolis, Ind.

[21] Appl. No.: 787,564

[22] Filed: Oct. 15, 1985

Related U.S. Application Data

[62] Division of Ser. No. 658,976, Oct. 9, 1984, Pat. No. 4,582,822.

[51] Int. Cl.$^4$ .................. C12N 1/20; C12P 19/60; C12R 1/03
[52] U.S. Cl. ...................... 435/75; 435/253; 435/825
[58] Field of Search .............. 435/126, 253, 825, 119, 435/74, 125, 75

[56] References Cited

U.S. PATENT DOCUMENTS

4,148,882  4/1979  Celmer et al. .................... 424/122
4,195,079  3/1980  Celmer et al. .................... 424/122
4,293,650 12/1981  Florent et al. .................... 435/119
4,407,946 10/1983  Labeda et al. .................... 435/75

OTHER PUBLICATIONS

J. Tone et al., "CP-47,433 and CP-47,434, New Polycyclic Ether Antibiotics Produced by a New Species of Actinomadura," and Current Chemotherapy and Infectious Disease, J. D. Nelson and C. Grassi, Eds., vol. I, American Society for Microbiology, Washington, D.C. 1980, pp. 469–470.

Nakamura et al., "A New Species of Actinomadura Producing a Polyether Antibiotic, Cationmycin," J. Antibiotics 36, 1468–1472 (1983).

Derwent Abstract No. 83–834403/49 of European Patent 95–154-A to Fujisawa Pharm. KK.

"Polyether Antibiotics, Naturally Occurring Acid Ionophores, vol. 1, Biology", J. W. Westley, Ed., Marcel Dekker Inc., New York, 1982, pp. viii–xi.

"Polyether Antibiotics, Naturally Occuring Acid Ionophores, vol. 2, Chemistry, J. W. Westley Ed., Marcel Dekker, Inc., New York, 1983, p. 197 and excerpts from pp. 223–224.

*Primary Examiner*—Thomas G. Wiseman
*Assistant Examiner*—Elizabeth C. Weimas
*Attorney, Agent, or Firm*—Nancy J. Harrison; Leroy Whitaker

[57] ABSTRACT

New polyether antibiotic A80190, its acyl and alkyl ester, acyl ester and urethane derivatives, and salts thereof, are useful antibacterial and anticoccidial agents and increase feed-utilization efficiency in animals. Methods of making A80190 by culture of *Actinomodura oligospora* NRRL 15877 and synergistic compositions of the A80190 compounds with nicarbazin, 4,4'-dinitrocarbanilide, certain napthalenamine and benzenamine compounds and metichlorpindol are also provided.

5 Claims, 4 Drawing Figures

ANTIBIOTIC A80190-PRODUCING ACTINOMADURA OLIGOSPORA AND PROCESS

This application is a division of application Ser. No. 658,976, filed Oct. 9, 1984, now U.S. Pat. No. 4,582,822, issued Apr. 15, 1986.

SUMMARY OF THE INVENTION

This invention relates to the new polyether antibiotic A80190 which is produced by *Actinomadura oligospora* strains NRRL 15877 and NRRL 15878. The structure of A80190 is shown in formula 1:

This invention also relates to acyl and alkyl ester and alkyl ether derivatives of A80190 and to the salts of A80190 and of the derivatives.

In addition this invention provides A80190 urethane derivatives of formula 2:

wherein R is —CONHR$_1$ and R$_1$ is alkyl, aryl, alkylaryl, arylalkyl, haloaryl, nitroaryl, haloarylalkyl, alkoxyaryl, aryloxyaryl, arylcycloalkyl, acylaryl and cycloalkyl; and salts of these derivatives.

Another aspect of this invention is the method of producing A80190 by culturing a strain of *Actinomadura oligospora*, NRRL 15877, under submerged aerobic fermentation conditions until a substantial level of the antibiotic is produced. A80190 is extracted from the fermentation broth and from the mycelium with polar organic solvents. A80190 is separated and further purified by techniques such as column chromatography.

Because *A. oligosporus* NRRL 15877 is a newly discovered strain, this invention further provides a biologically purified culture of this microorganism.

A80190 is useful as an antibacterial agent and an anticoccidial agent. It improves feed-utilization efficiency in ruminants and acts as a growth promotant in monogastric animals. In addition, A80190 has insecticidal, herbicidal and antiviral activity. Further, A80190 is useful as an ionophore. Methods and compositions pertaining to these uses are also provided.

This invention further relates to synergistic compositions of A80190, its acyl and alkyl ester, alkyl ether and urethane derivatives or a pharmaceutically acceptable salt thereof (an "A80190 compound"), together with a compound selected from nicarbazin, 4,4'-dinitrocarbanilide, metichlorpindol and certain naphthalenamine or benzenamine compounds. These compositions are useful in controlling coccidiosis in animals. Methods for using these compositions are another aspect of the invention.

DETAILED DESCRIPTION OF THE INVENTION

Improved antibiotics continue to be needed in the veterinary field. Enhancing growth promotion in animals is one desired feature of such antibiotics. Growth promotion can be achieved by reducing disease and by increasing feed-utilization efficiency.

Coccidiosis is a serious problem for the poultry industry. Coccidiosis results from infection by one or more species of Eimeria or Isopora. Improved anticoccidial agents are in demand because of the continuing economic losses due to coccidiosis.

Promoting growth by increasing feed-utilization efficiency is another ecomonically desirable objective of veterinary science. Of particular interest is growth promotion in ruminants, such as cattle.

The mechanism for utilizing the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA).

The relative efficiency of VFA utilization is connected to overall efficiency. Thus, although acetates and butyrates are used, propionates are used with greater efficiency. Also, the fermentation efficiency of propionate production is greater than that of butyrate and/or acetate. This is in addition to the utilization efficiency. A beneficial compound, therefore, stimulates animals to produce a higher proportion of propionates from carbohydrates, thereby increasing carbohydrate-utilization efficiency.

A80190 is a new member of the group of polyether antibiotics. Westley (John W. Westley, "Polyether Antibiotics: Naturally Occurring Acid Ionophores, Vol. 2, Chemistry," Marcel Dekker: New York, 1983) has separated existing polyethers by class and type. Using Westley's system, A80190 is a new member of the Class 1b, type (1), group of polyethers because it has one spiroketal system. Other members of this group include A-28695 A and B (U.S. Pat. No. 3,839,558); A204I and II (U.S. Pat. No. 3,705,238); A-32887 (U.S. Pat. No. 4,133,876); carriomycin; etheromycin; CP-47,434, RP37454 and the X-14868 antibiotics.

Characteristics of A80190

Figure 1:
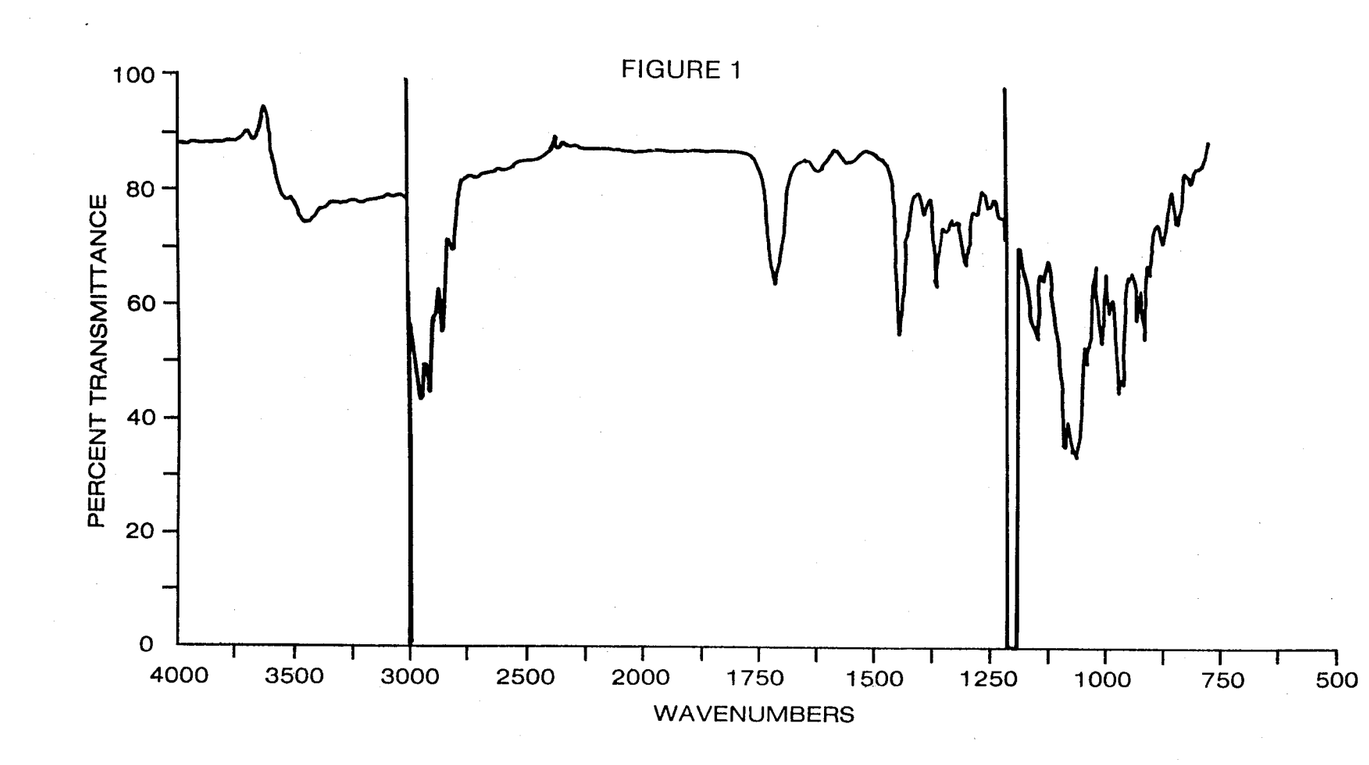
FIG. 1 shows the infrared absorption spectrum of A80190 in chloroform.

Antibiotic A80190 has been assigned structure 1 based on X-ray crystallographic studies. A80190 (in its free acid form) has the following characteristics:

State: white crystals (from acetone-water)
Mp: 98°–100° C. or 120°–122° C. (more frequently); probably varies with the degree of solvation
pKa: = 6.2 (66% aqueous dimethylformamide)
$[\alpha]^{25}D$: $-26°$ (c 1, CHCl$_3$)
Molecular weight: 828 (field desorption mass spectrometry)
Empirical formula: $C_{44}H_{76}O_{14}$
UV: no absorbance
IR: (CHCl$_3$) FIG. 1; shows absorption at the following frequencies (cm$^{-1}$): 3019, 2970, 2936, 2827, 1721, 1457, 1402, 1376, 1314, 1163, 1105, 1092, 1083, 1056, 1022, 1006, 989, 980, 945, 934, 917, 892 and 859
Elemental Analysis:

|  | Found | Calcd |
| --- | --- | --- |
| Carbon | 63.35 | 63.77 |
| Hydrogen | 9.17 | 9.18 |
| Oxygen | 27.10 | 27.05 |

Solubility: Insoluble in water; soluble in lower alcohols such as methanol, ketones such as acetone, esters such as ethyl acetate, halogenated hydrocarbons such as chloroform and hydrocarbons such as diethyl ether, benezene, toluene and warm hexane.

A80190 has an acid function capable of forming salts and ester derivatives and has at least one hydroxyl group which can be esterified or which can form ether derivatives. The acyl and alkyl ester and alkyl ether derivatives of A80190, the urethane derivatives of formula 2, and the pharmaceutically-acceptable salts of A80190 and of these derivatives are also useful as antibiotics and as agents which increase feed-utilization efficiency.

The term "acyl" means a C$_1$ to C$_7$, preferably a C$_1$ to C$_4$, alkanoic acid moiety, i.e., radicals of the formula wherein $R_{1a}$ is C$_1$ to C$_6$-alkyl or hydrogen, e.g., formyl, acetyl, propionyl, butyryl and the like.

The term "cycloalkyl" means cyclic hydrocarbon groups containing from 3 to 7 carbon atoms, such as, cyclopropyl, cyclobutyl, cyclohexyl and the like, cyclohexyl being preferred. The cycloalkyl group may be substituted by an aryl residue, as defined herein, to form an arylcycloalkyl residue, e.g., 2-(phenyl)cyclopropyl.

The term "alkoxy" means a C$_1$ to C$_7$ lower alkyl group having an oxygen function substituted therein, such as methoxy, ethoxy, propoxy and the like.

The term "aryl" denotes an aromatic residue derived by the removal of a hydrogen atom from an aromatic hydrocarbon, such as, for example, phenyl, pyridyl or furyl, especially phenyl. The "aryl" residue may be substituted by various groups. A substitutent on a phenyl nucleus is preferably on the 4-position. Examples are 4-alkylaryl, e.g., 4-methylphenyl (4-tolyl); 4-halophenyl, e.g., 4-chlorophenyl; 4-nitrophenyl; 4-aryloxy-aryl, e.g., 4-phenoxyphenyl; 4-alkoxyphenyl, e.g., 4-methoxyphenyl; and 4-(alkyl-carbonyl)phenyl, e.g., 4-(methylcarbonyl)phenyl or 4-(phenylcarbonyl)phenyl.

The term "alkyl" means a C$_1$ to C$_7$ straight or branched chain hydrocarbon, preferably a C$_1$ to C$_4$ hydrocarbon, carbon, e.g., methyl, ethyl, propyl, isopropyl, n-butyl, etc. The alkyl group may be substituted by an aryl residue, as defined supra, to form an arylalkyl residue, e.g., phenylethyl or 2-phenylethyl or by a haloaryl residue to form a haloarylalkyl residue, e.g., 4-bromophenethyl.

The salts of A80190 and of its derivatives are useful for separating and purifying the antibiotics. The pharmaceutically-acceptable salts are particularly useful. Examples of salts are the alkali-metal, alkaline-earth-metal and amine salts of A80190 and of its derivatives.

Representative and suitable alkali-metal and alkaline-earth metal salts of A80190 include the sodium, potassium, lithium, cesium, rubidium, barium, calcium and magnesium salts. Suitable amine salts of A80190 include the ammonium and the primary, secondary, and tertiary C$_1$–C$_4$-alkylammonium and hydroxy-C$_2$–C$_4$-alkylammonium salts. Illustrative amine salts include those formed by reaction of A80190 with ammonium hydroxide, methylamine, sec-butylamine, isopropylamine, diethylamine, di-isopropylamine, ethanolamine, triethylamine, 3-amino-1-propanol and the like.

It is well known in the veterinary pharmaceutical art that the form of an antibiotic is not ordinarily of great significance when treating an animal with the antibiotic. In most cases, conditions within the animal change the drug to a form other than that in which it was administered. The salt form in which it may be administered is, therefore, not of great significance. The salt form may, however, be chosen for reasons of economy, convenience, and toxicity.

Antibiotic A80190 is produced by culturing an A80190-producing strain of *Actinomadura oligospora* under submerged aerobic conditions in a suitable culture medium until substantial antibiotic activity is produced. The antibiotic is recovered using various isolation and purification procedures understood in the art.

The new microorganism of this invention, which produces antibiotic A80190, was isolated from a soil sample from India. Subsequently, a substantially improved variant which produces increased amounts of A80190 was isolated by LaVerne D. Boeck. The variant is the subject of Boeck's copending application, attorney docket No. X-6586 entitled PROCESS FOR PRODUCING ANTIBIOTIC A80190, Ser. No. filed 658977 Oct. 4, 1984.

Cultures of these two A80190-producing organisms have been deposited and made part of the stock culture collection of the Northern Regional Research Center, Agricultural Research, North Central Region, 1815 North University Street, Peoria, Illinois, 61604, from which they are available to the public under the accession numbers NRRL 15877 (parent strain) and NRRL 15878 (the variant strain).

Taxonomic studies of the variant were carried out by Frederick P. Mertz of the Lilly Research Laboratories. Based on these studies, the two new organisms are classified as members of a new species of the genus Actinomadura for which the name *Actinomadura oligospora* sp. nov. is proposed. This classification is based on direct laboratory comparisons with similar species and examination of published descriptions [M. Goodfellow and G. Alderson, "Numerical Taxonomy of Actinomadura and Related Actinomycetes," J. Gen. Microbiol. 112:95-111 (1970); M. Goodfellow and K. P. Schaal, "Identification Methods for Nocardia, Actinomadura and Rhodococcus," p. 261-276 In F. A. Skinner and D. W. Lovelock (ed.), "Identification Methods for Microbiologists," 2nd ed., The Society for Applied Microbiology Technical Series No. 14, Academic Press, New York, 1979; L. H. Huang, "Actinomadura macra sp. nov., the Producer of Antibiotics CP-47,433 and CP-47,434," Int. J. Syst. Bacteriol. 30:565-568 (1980); and H. A. Lechevalier and M. P. Lechevalier, "A Critical Evaluation of the Genera of Aerobic Actinomycetes," p. 393-405, In H. Prauser (ed.), "The Actinomycetales," Gustav Fischer Verlag, Jena].

Methods Used

The methods recommended by the International Streptomyces Project (ISP) for the characterization of Streptomyces species [E. B. Shirling and D. Gottlieb, "Methods for Characterization of Streptomyces Species," Int. J. Syst. Bacteriol. 16:313-340 (1966)] have been followed along with certain supplementary tests (D. J. Blazevic and G. M. Ederer, "Principles of Biochemical Tests in Diagnostic Microbiology," John Wiley and Sons, Inc., New York, 1975).

Carbon utilization was determined with ISP No. 9 basal medium to which filter-sterilized carbon sources were added to equal a final concentration of 1.0 percent. Plates were incubated at 30° C. and read after 14 days.

Melanoid pigment production (chromogenicity) was determined with ISP No. 1 (tryptone-yeast extract broth), ISP No. 6 (peptone-yeast extract iron agar), ISP No. 7 (tyrosine agar) and modified ISP No. 7 which has tyrosine removed.

Starch hydrolysis was determined by testing for the presence of starch with iodine on ISP No. 4 (inorganic salts-starch agar) plates (See Blazevic and Ederer, supra).

Morphology was studied using an optical light microscope. A scanning electron microscope (SEM) was used to study the spore surface ornamentation.

NaCl tolerance was measured by adding NaCl to ISP No. 2 agar to equal the concentration desired.

ICSS-NBS Centroid Color Charts, standard sample No. 2106 (National Bureau of Standards, 1958, U.S. Department of Commerce, Washington, D.C.) and the Color Harmony Manual (4th ed., Container Corporation of America, Chicago, Illinois, 1958) were used to assign color names.

The isomers of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates," Appl. Microbiol. 12:421-423 (1964)] and of Lechevalier [M. P. Lechevalier, "Identification of Aerobic Actinomycetes of Clinical Importance," J. Lab. Clin. Med. 71:934-944 (1968)].

Resistance to lysozyme was measured by methods recommended by Gordon [R. E. Gordon and D. A. Barnett, "Resistance to Rifampin and Lysozyme of Strains of Some Species of Mycobacterium and Nocardia as a Taxonomic Tool," Int. J. Syst. Bacteriol. 27, 176-178 (1977)].

Resistance to antibiotics was measured by padding antibiotic sensitivity discs onto the surface of seeded ISP No. 2 agar plates.

Phosphatase and urease were determined by methods described by Blazevic, supra.

Mycolic acids were determined by a method based on techniques described by Minnikin [D. E. Minnikin, L. Alshamaony and M. Goodfellow, "Differentiation of Mycobacterium, Nocardia, and Related Taxa by Thin-Layer Chromatographic Analysis of Whole-organism Methanolysates," J. Gen. Microbiol. 88:200-204 (1975).

Phospholipid analysis was performed as described by Lechevalier [M. P. Lechevalier, C. De Bievre and H. Lechevalier, "Chemotaxonomy of Aerobic Actinomycetes: Phospholipid Composition," Biochemical Systematics and Ecology 5, 249-260 (1977)].

Cultural Characteristics

Growth of the organism was generally poor on chemically defined media but better on complex organic media. Aerial mycelia were absent except for trace amounts on ISP No. 4 and sodium butyrate agar. When spores were present, their color was oyster white in the Tresner and Backus System [H. D. Tresner and E. J. Backus, "System of Color Wheels for Streptomycete Taxonomy," Appl. Microbiol. 11:335-338 (1956)]. The color of the reverse side was yellowish gray to brown. No soluble pigments were produced, except for the production of a very light brown soluble pigment in ISP No. 2 and a dark brown soluble pigment in yeast-dextrose agar. Table I presents these cultural characteristics.

TABLE I

Cultural Characteristics of NRRL 15878 and
A. macra on Various Agar Media[a]

| Agar Media | NRRL 15878 | A. macra |
|---|---|---|
| ISP No. 2 | G: Good (moist surface)<br>R: 61.gy.Br<br>Am: None<br>Sp: Very light brown | Abundant (39.gy.r0)<br>43.m.rBr → 56.deep Br.<br>None<br>Very light brown |
| ISP No. 3 | G: Poor<br>R: 5.m.Pink 93.y Gray<br>Am: Trace: b White few scattered individual clumps<br>SP: None | Fair<br><br>None<br><br>None |
| ISP No. 4 | G: Poor<br>R: 93.y Gray<br>Am: Trace: b White few scattered individual clumps<br>SP: None | Fair to poor<br>5 m. Pink<br>None<br><br>None |
| ISP No. 5 | G: Poor<br>R: 93.y Gray<br>Am: None<br>Sp: None | Good<br>48.v.0<br>None<br>None |
| ISP No. 7 | G: Poor (moist surface)<br>R: 79.1.gy.y.Br<br>Am: None<br>Sp: Light-brown | Fair<br>48.v.0<br>None<br>None |
| Czapek's | G: Fair<br>R: 93.y Gray<br>Am: None<br>Sp: None | Fair<br>93.y Gray<br>None<br>None |
| Emerson's | G: Good (edges peeled back)<br>R: 77.m.yBr<br>Am: None<br>Sp: None | Good<br><br>267. Black<br>Trace: 5fe 1.gy.rBr<br>None |
| Glucose Aspara-gine | G: Good (moist surface)<br>R: 90.gy.Y<br>Am: None<br>Sp: None | Good<br>26.s.y Pink<br>Fair: a White → 7ca 1.y Pink<br>None |
| Tomato-paste Oatmeal | G: Abundant (moist surface)<br>R: 79.1.gy.y.Br<br>Am: None<br>Sp: None | Good<br><br>39.gy.r0<br>Trace: 2 White (edges only)<br>None |
| Yeast-dextrose | G: Abundant (moist surface)<br>R: 81.d.gy.y Br<br>Am: None<br>Sp: Dark-brown | Abundant (moist surface)<br>59.d.Br<br>Slight trace: Gray<br>Dark-brown |
| Sodium Butyrate | G: Good<br>R: 78.d.yB 93.y Gray<br>Am: Fair: b White<br>Sp: None | Fair<br><br>None<br>None |
| Calcium Malate | G: Fair<br>R: 93.y Gray<br>Am: None<br>Sp: None | Fair<br>26.s.y Pink<br>None<br>None |

[a] G = growth
R = reverse
Am = aerial mycelium
Sp = soluble pigment

Morphological Characteristics

Spore chains were sparsely produced on ISP No. 4 and sodium butyrate agar. Sporophores contained approximately 10 spores per chain, and were generally flexuous as in the Rectus-flexibilis (RF) configuration. However, hooked sporophores were also observed. The aerial hyphae had a tendency to clump together. Spore shape was oblong and ranged in size from 0.5–0.7 $\mu$m. by 0.9–1.3 $\mu$m. The average spore size measured 1.1 by 0.6 $\mu$m. The average spore surface ornamentation was smooth.

Physiological Characteristics

Table II lists the carbohydrate utilization pattern of the strain as compared to that of A. macra. ISP medium No. 9 was used as a basal medium. The addition of vitamin $B_1$ or the use of Luedemann's medium [G. M. Luedemann and B. Brodsky, "*Micromonospora carbonacea* sp. n., an Everinomicin-producing Organism," *Antimicrob. Agents Chemother.* 1964, 47–52] produced slightly better growth, but no change in carbon utilization. Adonitol, cellobiose, glucose, and ribose were utilized. Questionable utilization was noted with fructose and xylose. Arabinose, cellulose, dextran, galactose, i-inositol, inulin, lactose, mannitol, mannose, melizitose, melibiose, raffinose, rhamnose, salicin, sucrose, trehalose, and xylitol were not utilized for growth.

TABLE II

Carbon Utilization Pattern of NRRL 15878 and A. macra[a]

| Carbon Source | NRRL 15878 | A. macra |
|---|---|---|
| control | − | − |
| adonitol | + | − |
| L-arabinose | − | − |
| cellobiose | + | − |
| cellulose | − | ND |
| dextran | − | ND |
| D-fructose | ± | − |
| D-galactose | − | ± |
| D-glucose | + | + |
| i-inositol | − | ± |
| inulin | − | ND |
| D-lactose | − | − |
| mannitol | − | − |
| D-mannose | − | − |
| D-melezitose | − | − |
| D-melibiose | − | − |
| raffinose | − | − |
| L-rhamnose | − | − |
| ribose | + | ± |
| salicin | − | − |
| sucrose | − | + |
| trehalose | − | + |
| xylitol | − | ND |
| D-xylose | ± | ± |

[a] + = utilized,
− = not utilized,
± doubtful if utilized,
ND = not done

Table III lists the resistance of the strain to various antibiotics at the concentrations indicated and compares it to that of *A. macral.*

TABLE III

Resistance to Antibiotics by NRRL 15878 and A. macra[a]

| Antibiotic | Concentration | NRRL 15878 | A. macra |
|---|---|---|---|
| Bacitracin | 10 units | + | − |
| Cephalothin | 30 $\mu$g | + | + |
| Gentamicin | 10 $\mu$g | − | − |
| Lincomycin | 2 $\mu$g | + | + |
| Neomycin | 30 $\mu$g | − | − |
| Oleandomycin | 15 $\mu$g | − | |
| Pencillin G | 10 units | + | + |
| Rifampin | 5 $\mu$g | + | + |
| Streptomycin | 10 $\mu$g | − | + |
| Tetracycline | 30 $\mu$g | − | − |
| Tobramycin | 10 $\mu$g | − | − |

TABLE III-continued

| Resistance to Antibiotics by NRRL 15878 and *A. macra*[a] | | | |
|---|---|---|---|
| Antibiotic | Concentration | NRRL 15878 | *A. macra* |
| Vancomycin | 30 μg | − | − |

[a] + = resistant (no zones of inhibition)
− = sensitive (zones of inhibition)

NRRL 15878 grew at temperatures from 15°–42° C., and tolerated up to 2 percent NaCl. It produced catalase, phosphatase and urease.

NRRL 15878 degraded casein, DNA, esculin, and gelatin, but not adenine, calcium malate, chitin, elastin, guanine, hippurate, hypoxanthine, keratin, starch, testosterone, tyrosine or xanthine.

Cell-wall Analysis

Hydrolyzed whole cells contained the meso isomer of diaminopimelic acid. Sugars present in whole cell hydrolysates were as follows: glucose, mannose, madurose, and ribose. The cell-wall type according to Becker, supra, is type III, and the sugar pattern is type B (Lechevalier, 1968). A qualitative analysis of whole-cell methanolysates for mycolic acids yielded questionable results. It is doubtful that the culture contains mycolic acids. A type PI phospholipid pattern was found. Type PI contains no nitrogenous phospholipids and is characteristic of the genus Actinomadura (Lechevalier, 1977).

Identity of the Strain

NRRL 15878 has a Type III cell wall, Type B whole-cell sugar pattern, and a Type PI phospholipid pattern. This chemotaxonomic information plus its general cultural characteristics are consistent with the assignment of the strain to the genus Actinomadura Lechevalier and Lechevalier (Lechevalier, 1970).

Comparison of its characteristics to those in published descriptions of known species of Actinomadura show that the culture is similar to *A. pelletieri* (Laveran 1906) Lechevalier and Lechevalier, 1970 and to *A. macra* (Huang, 1980).

The culture resembles *Actinomadura pelletieri* mainly by the absence, or at least the rare occurrence, of aerial mycelia. Morphology of sporophores, when produced, is similar to that described in the literature (Goodfellow, 1979). The two cultures also possess a number of physiological characteristics in common. However, the cultural and physiological differences are sufficient to separate them as distinct species.

According to Lechevalier (1970), *A. pelletieri* is represented exclusively by a group of clinical isolates. The original description of *A. pelletieri* by Gordon [R. E. Gordon, "Some Criteria for the Recognition of *Nocardia madurae* (Vincent) Blanchard," J. Gen. Microbiol 45:355–364 (1966)] describes it as being a bright red culture. NRRL 15878 does not produce this pigment. *A. pelletieri* degrades elastin, hypoxanthin, keratin, tyrosine, utilizes trehalose, reduces nitrate, and grows at 45° C.; but NRRL 15878 does not have these characteristics. NRRL 15878 utilizes adonitol and cellobiose, degrades esculin and DNA, and is resistant to lysozyme; but *A. pelletieri* does not have these characteristics. The new culture is, therefore, considered to be a different species than *A. pelletieri*.

Because of the culture's similarity to *A. macra*, simultaneous laboratory comparisons were made. NRRL 15878 and *A. macra* share many properties. Both are unable to degrade adenine, calcium-malate, chitin, elastin, guanine, keratin, starch, testosterone, tyrosine, and xanthine. Neither produces H₂S or melanoid pigments. Both cultures degrade casein, DNA and gelatin, produce catalase and phosphatase, and synthesize a polyether antibiotic. They have the same tolerance to NaCl; both grow on sodium butyrate; and they have the same cell-wall type. *A. macra* and NRRL 15878 differ in carbon-utilization pattern, esculin and hypoxanthine degradation, resistance to antibiotics, temperature range, urease production, and the reduction of nitrate.

*A. macra* and NRRL 15878 share many cultural characteristics, notably the absence of aerial mycelia. However, there are significant differences. The reverse side of NRRL 15878 is gray to a yellowish brown; *A. macra* on many media produces a red color. This distinction is most clearly seen on glucose-asparagine agar. On this medium *A. macra* produces a pink aerial growth, whereas NRRL 15878 produces none. These cultural comparisons are shown in Table I.

The morphology of NRRL 15878 is similar to that of *A. macra*. Both have poorly developed aerial mycelia that belongs in the Rectus-flexibilis (RF) section of Pridham [T. G. Pridham, C. W. Hesseltine, and R. C. Benedict, "Guide for the Classification of Streptomycetes According to Selected Groups," Appl. Microbio. 1 6:52–79 (1957). Spore surface ornamentation is smooth.

The differences and similarities between NRRL 15878 and *A. macra* are summarized in Table IV.

TABLE IV

| Summary Comparison of NRRL 15878 and *A. macra* | |
|---|---|
| Similarities | Differences |
| Morphology | Antibiotic resistance |
| Physiological properties | Carbon-utilization pattern |
| Polyether synthesis | Cultural characteristics |
| Scarcity of aerial hyphae | Degradation of esculin |
| | Degradation of hypoxanthine |
| | Nitrate reduction |
| | Spore shape and size |
| | Temperature range |
| | Urease production |

Table V shows these similarities and differences in greater detail.

TABLE V

| Comparison of NRRL 15878 and *A. macra* | | |
|---|---|---|
| Test | NRRL 15878 | *A. macra* |
| Aerial hyphae formation | rare | rare |
| Carbon-utilization pattern | different (see Table II) | |
| Catalase degradation of: | | |
| adenine | − | − |
| calcium malate | − | − |
| casein | + | + |
| chitin | − | − |
| DNA | + | + |
| elastin | − | − |
| esculin | + | − |
| gelatin | + | + |
| guanine | − | − |
| hypoxanthine | − | + |
| keratin | − | − |
| starch | − | − |
| testosterone | − | − |
| tyrosine | − | − |
| xanthine | − | − |
| Growth in liquid media | colorless | red-orange |
| Growth on Na butyrate | + | + |
| H₂S production | − | − |
| Melanoid pigments | − | − |
| NaCl tolerance | 2 percent | 2 percent |
| Nitrate reduction | − | + |

TABLE V-continued

| | Comparison of NRRL 15878 and *A. macra* | |
|---|---|---|
| Test | NRRL 15878 | *A. macra* |
| Phosphatase | + | + |
| Polyether synthesis | + | + |
| Resistance pattern to antibiotics | different (see Table III) | |
| Resistance to lysozyme | + | ND |
| Reverse side color | gray → brown | brown → orange |
| Soluble pigment | brown | brown |
| Spore chains | RF | RF |
| Spore surface | smooth | smooth |
| Temperature range | 15–42° | 15–37° |
| Urease production | + | − |
| Spore shape | oblong | oval |
| Spore size | 0.5–0.7 × 0.9–1.3 µm | 0.8–1.0 × 1.2–2.0 µm |

These comparisons indicate that the NRRL 15877 and NRRL 15878 cultures are significantly different from other species of Actinomadura and represent strains of a new species for which the name *Actinomadura oligosporas* sp. nov. is proposed. The specific epithet (O.ligo.spor.as: L. Adj. oligo few, L.n. sporas spored, oligosporas few spored) refers to the relative absence of sporophores in the organism. Strain NRRL 15878 is the type strain of *A. oligosporas*.

As is the case with other organisms, the characteristics of the A80190-producing culture of this invention, *Actinomadura oligosporas* NRRL 15877, are subject to variation. Recombinants, mutants or variants of the strain may be obtained by methods in the art. For example, mutants can be obtained by treatment with various known physical and chemical mutagens such as ultraviolet light, X rays, gamma rays and chemicals such as N-methyl-N'-nitro-N-nitrosoguanidine. Natural and induced variants, mutants and recombinants of *Actinomadura oligosporus* NRRL 15877 which retain the characteristic of A80190 production are considered part of this invention.

The culture medium used to grow the *Actinomadura oligosporus* cultures can be any one of a number of media. For economy in production, optimal yield, and ease of product isolation, however, certain culture media are preferred. Thus, for example, a preferred carbohydrate source in large-scale fermentation is glucose, although ribose, xylose, fructose, galactose, mannose, mannitol, potato dextrin and the like can also be used. Glycerol and lipids support little or no growth or antibiotic production when used as the primary carbon source. In combination with glucose, they enhance biomass, but depress antibiotic production.

A preferred nitrogen source is collagen hydrolysate, although enzyme-hydrolyzed casein, meat peptones, fish meal, liver meal, and the like are also useful. Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.2 ml/L) of an antifoam agent such as polypropylene glycol may be added to large scale fermentation media if needed.

For production of substantial quantities of antibiotic A80190, submerged aerobic fermentation in tanks is preferred. Small quantities of A80190 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80190 is produced by the A80190-producing organism when grown at temperatures between about 25° and about 37° C. An optimum temperature for A80190 production appears to be about 30°–32° C.

As is customary in submerged aerobic culture processes, sterile air is blown into the vessel from the bottom while the medium is stirred with conventional turbine impellors. The maximum oxygen uptake of the fermentation under the conditions used thus far has not exceeded about 0.2 mM/L/minute. In a fully baffled 165-liter fermentor containing approximately 115 liters of broth, an aeration rate of 0.125 v/v/m with an agitation rate of 200 rpm is sufficient to maintain the level of dissolved oxygen at or above 30% of saturation.

Production of antibiotic A80190 can be followed during the fermentation by testing samples of the broth for antibiotic activity against organisms known to be sensitive to the antibiotic. One assay organism useful in testing A80190 is *Bacillus subtilis* ATCC 6633. The bioassay is conveniently performed by the agar-well plate test.

Following its production under submerged aerobic fermentation conditions, A80190 can be recovered from the fermentation medium by methods used in the fermentation art. The antibiotic activity produced during fermentation of the A80190-producing organism occurs both in the filtered broth and in the mycelial mass. Maximum recovery of A80190 is accomplished, therefore, by initially filtering the medium to separate the broth from the mycelial mass. The filtered broth and the mycelial mass can then be purified separately to give their respective portion of A80190. A variety of techniques may be used in this purification. A preferred technique for purification of the filtered broth involves adjusting it to a pH of about 9 and extracting with a suitable solvent such as, for example, ethyl acetate. The extracting solvent can then be evaporated under vacuum to give the broth portion of A80190. A preferred method of purifying the mycelial mass is to extract the separated mycelial filter cake with a suitable solvent such as, for example, methanol or acetone. The extracting solvent is then evaporated under vacuum to give a concentrated aqueous solution. This aqueous solution is then adjusted to a pH of about 9 and is extracted with a suitable solvent such as, for example, ehtyl acetate. The extracting solvent is then concentrated under vacuum to give the mycelial portion of A80190. The broth and mycelial portions of the A-80190 complex are further purified by similar procedures. A preferred procedure involves silica gel chromatography.

Alternatively, the culture solids, including medium constituents and mycelium can be used without extraction or separation, but preferably after removal of water, as a source of A80190. For example, after production of A80190, the whole fermentation broth can be dried by lyophilization, by drum-drying, or by azeotropic distillation and drying. The dried broth is then mixed directly into feed premix.

The alkali-metal and alkaline-earth-metal cationic salts of A80190 are prepared according to procedures commonly used for the preparation of cationic salts. For example, the free acid of A80190 is dissolved in a suitable solvent such as acetone; a ⅓ volume of water is added; and this solution is adjusted to a pH of about 9 to 10 with the base of the desired cationic salt (e.g. NaOH, KOH). The salt thus formed can be isolated by routine methods, such as filtration or evaporation of the solvent.

A preferred method of forming salts is to dissolve A80190 (acid form) in a water-immiscible solvent such as ethyl acetate, add an equal volume of water, and adjust the mixture to pH 10 with the corresponding cationic base (e.g. NaOH, KOH, etc.) The separated organic phase is washed with water and concentrated to dryness. The residue is lyophilized from dioxane. The salt can be crystallized from an appropriate solvent, such as pentane.

The salts formed with organic amines can be prepared similarly. For example, the gaseous or liquid amine can be added to a solution of A80190 in a suitable solvent such as acetone; the solvent and excess amine can be removed by evaporation.

A80190 acyl-ester derivatives are prepared by treating A80190 with a corresponding acid anhydride or acid chloride. Esterification occurs at one of the A80190 hydroxyl groups. Such esters are typically prepared by reacting A80190 with, for example, the corresponding acid anhydride at room temperature.

A80190 alkyl ester derivatives are prepared by esterification of the carboxyl group, using standard procedures. The A80190 alkyl ester derivatives are typically less active when tested in vitro. When administered to an animal, however, such esters can act as pro drugs which are converted to A80190 in vivo.

The alkyl ether derivatives of A80190 are those compounds wherein one or more of the hydroxyl groups has been replaced by a YR group wherein:
Y represents O or S; and
R represents $C_1$-$C_6$-alkyl, $C_1$-$C_4$-alkoxy-$C_2$-$C_5$-alkyl, $C_1$-$C_4$-alkoxycarbonyl-$C_2$-$C_5$-alkyl, amino-$C_2$-$C_5$-alkyl, mercapto-$C_2$-$C_5$-alkyl, hydroxyalkyl, haloalkyl, or
$(R')_m$-phenyl$(CH2)_n$—,
wherein R' represents $C_1$-$C_4$-alkyl, $C_1$-$C_4$-alkoxy or hyoroxy;
m represents 0-2; and
n represents 0-3.

The terms alkyl and alkoxy have the meaning discussed supra, but are limited to the number of carbon atoms specified.

The term "hydroxyalkyl" refers either to a monohydroxy-$C_2$-$C_5$-alkyl moiety or, when Y is O, to the 2,3-dihydroxyprop-1-yl moiety.

The term "haloalkyl" refers to a $C_2$-$C_5$-alkyl moiety having from one to three halogen substituents, selected from the group consisting of bromine, chlorine, and fluorine. When the alkyl moiety is dihalo- or trihalo-substituted, the halo-substituents must be the same halogen moiety.

Preferred A80190 ether derivatives are those compounds wherein Y represents O and R represents $C_1$ to $C_6$ alkyl. The ether derivatives are prepared by reacting A80190, or a salt thereof, with a corresponding primary alcohol or thiol.

With some of the starting alcohols or thiols it may be necessary to add an acid catalyst to the reaction. Suitable catalysts include hydrochloric acid, sulfuric acid, methanesulfonic acid, benzenesulfonic acid, toluenesulfonic acid, selenium dioxide, and boron trifluoride.

A solvent such as, for example, water, acetone, benzene, ether, tetrahydrofuran, or dioxane may be added to facilitate the reaction. Reactions generally occur at room temperature, although higher temperatures may be used.

Although ordinary reaction work-up procedures are sometimes sufficient, additional purification may be required to obtain the compounds of this invention. Such purification may be accomplished by well-known methods, such as, for example, column chromatography, thin-layer chromatography, fractional crystallization and the like.

The A80190 urethane derivatives of formula 2 can be prepared by treating A80190 or an A80190 salt with an isocyanate of formula 3

$$R-NCO \qquad 3$$

wherein R is as defined supra.

Preferably, a salt of A80190, in particular the sodium salt, is used. The isocyanate of formula 3 should be added in slight excess, e.g., about 10% excess, in order to form the mono derivative in optimum quantity. The reaction is preferably carried out in an inert solvent such as a chlorinated hydrocarbon, e.g., carbon tetrachloride, methylene chloride or chloroform, ether, ethyl acetate or in an aromatic hydrocarbon solvent such as benzene or toluene. The reaction temperature is not critical but can be between above 0° C. and the boiling point of the reaction mixture, but is preferably about room temperature.

The A80190 compounds inhibit the growth of bacteria and fungi which are pathogenic to animal and plant life. The inhibitory activity of A80190 is illustrated in Table VI. Activity was measured by the conventional disc-diffusion method (6-mm pads were dipped in solutions containing 1 mg of compound per ml of solution; pads were placed on agar plates seeded with test organism).

TABLE VI

Antibacterial Activity of A80190

| Test Organism | Zone of Inhibition (mm diameter) |
|---|---|
| *Staphylococcus aureus* | 17 |
| *Bacillus subtilis* | 23 |
| *Micrococcus luteus* | 20 |
| *Mycobacterium avium* | 21 |
| *Saccharomyces pastorianus* | 10 |
| *Neurospora crassa* | 14 |
| *Candida albicans* | 14 |

One important aspect of the antimicrobial activity of A80190 compounds relates to their activity against anaerobic bacteria. The minimal inhibitory concentrations (MIC's) at which A80190 inhibits various anaerobic bacteria, as determined by standard agar-dilution assay, are summarized in Table VII. End points were read after 24-hour incubation.

TABLE VII

| Susceptibility of Anaerobic Bacterial Isolates to A80190 | |
|---|---|
| Anaerobic Bacteria | MIC (μg/ml) |
| *Clostridium difficile* 2994 | <0.5 |
| *Clostridium perfringens* 81 | <0.5 |
| *Clostridium septicum* 1128 | <0.5 |
| *Eubacterium aerofaciens* 1235 | <0.5 |
| *Peptococcus asaccharolyticus* 1302 | 1 |
| *Petococcus prevoti* 1281 | <0.5 |
| *Peptostreptococcus anaerobius* 1428 | 1 |
| *Peptostreptococcus intermedius* 1624 | 1 |
| *Propionibacterium acnes* 79 | 1 |
| *Bacteroides fragilis* 111 | >128 |
| *Bacteroides fragilis* 1877 | >128 |
| *Bacteroides fragilis* 1936B | >128 |
| *Bacteroides thetaiotaomicron* 1438 | >128 |
| *Bacteroides melaninogenicus* 1856/28 | >128 |
| *Bacteroides melaninogenicus* 2736 | >128 |
| *Bacteroides vulgatis* 1211 | 16 |
| *Bacteroides corrodens* 1874 | >128 |
| *Fusobacterium symbiosum* 1470 | 8 |
| *Fusobacterium necrophorum* 6054A | 16 |

Anticoccidial activity is an important property of the A80190 compounds. Table VIII summarizes the results of an in vitro tissue culture screen of A-80190 compounds vs. *Eimeria tenella*.

TABLE VIII

Activity of A80190 Compounds vs. *Eimeria tenella* In Vitro

| | Concentration (μg/ml) | | | | |
|---|---|---|---|---|---|
| Compound | 5 | 1 | 0.2 | 0.04 | 0.008 |
| A80190 | C[a] | C | A | A | A |
| Acetyl A80190 | A | A | A | A | N |
| Propionyl A80190 | A | A | A | A | S |

[a] C = cytotoxic
A = active
S = slightly active
N = not active

For treating coccidiosis in poultry, a nontoxic anticoccidial amount of an A80190 compound is administered to infected or susceptible birds, preferably orally on a daily basis. The A80190 compound can be supplied in many ways, but it is most conveniently supplied with a pharmaceutically acceptable carrier, preferably the feed ingested by the birds. Although a variety of factors must be considered in determining an appropriate concentration of A80190 compound, the rates of administration are generally in the range of about 2 to about 100 ppm in the feed and are preferably in the range of about 15 to about 50 ppm of feed ration. In another aspect, this invention relates to compositions for treating coccidiosis comprising an effective amount of an A80190 compound for treating coccidiosis, together with a suitable vehicle.

Compositions for controlling coccidiosis in poultry of this invention comprise:

(1)
  (a) an A80190 compound of formula 1;
  (b) an A80190 urethane derivative of formula 2 or
  (c) a pharmaceutically acceptable salt of an (a) or (b) compound;
in combination with
(2) a compound selected from the group consisting of
  (a) nicarbazin,
  (b) 4,4'-dinitrocarbanilide,
  (c) a napthalenamine compound of formula 4:

wherein:
$R^2$ is $C_1$-$C_4$ alkyl;
$R^3$ is halogen, $C_1$-$C_4$ fluoroalkyl, $C_1$-$C_4$ fluoroalky or $C_1$-$C_4$ fluoroalkylthio;
$R^4$ is halogen;
$R^5$ is hydrogen or halogen;
m is 0, 1 or 2; and
n is 0 or 1;
  with the proviso that, when an $R^4$ substituent exists, it is at other than the 2-position;

(d) a benzenamine selected from 2,4-dinitro-N-4-(trifluoromethoxy)phenyl]-6-(trifluoromethyl)benzenamine; 2,4-dinitro-N-[4-(1,1,2,2-tetrafluoroethoxy)phenyl]-6-(trifluoromethyl)benzenamine or 2,4-dinitro-N-[4-(pentafluoroethoxy)phenyl]-6-(trifluoromethyl)benzenamine;

(e) metichlorpindol; or (f) a pharmaceutically acceptable salt of an (a)-(e) compound.

In formula 4, $C_1$-$C_4$ alkyl includes methyl, ethyl, n-propyl, isopropyl, n-butyl, sec.-butyl, isobutyl, t-butyl, and the like.

The term "halogen" represents fluorine, chlorine, bromine and iodine.

$C_1$-$C_4$ Fluoroalkyl is a $C_1$-$C_4$ alkyl group bearing one fluorine atoms. Such fluoroalkyl groups include trifluoromethyl, 1,1,2,2-tetrafluoroethyl, pentafluoroethyl, 1,2,3,3-tetrafluoropropyl, nonafluorobutyl, and the like.

$C_1$-$C_4$ Fluoroalkoxy is a $C_1$-$C_4$ alkoxy group bearing one or more fluorine atoms. Such fluoroalkoxy groups include difluoromethoxy, trifluoromethoxy, 1-fluoroethoxy, 1,1,2,2-tetrafluoroethoxy, pentafluoroethoxy, 1,2,2,3,3-pentafluoropropoxy, heptafluoropropoxy, 4,4,4-trifluorobutoxy, and the like.

$C_1$-$C_4$ Fluoroalkylthio is a $C_1$-$C_4$ alkylthio group bearing one or more fluorine atoms. Such fluoroalkylthio groups include trifluoromethylthio, 1,1,2,2-tetrafluoroethylthio, pentafluoroethylthio, 4,4,4-trifluorobutylthio, and the like.

Preferred formula 4 compounds are those wherein m and n are 0 and $R^5$ is hydrogen.

Typical formula 4 compounds are:
4-Fluoro-N-[2,4-dinitro-6-(trifluoromethyl)phenyl]-1-naphthalenamine
4-Iodo-N-[2,4dinitro-6-(trifluoromethyl)phenyl]-1-naphthalenamine
4-Trifluoromethyl-N-[2,4-dinitro-6-(trifluoromethyl)phenyl[-1-naphthalenamine
4-Pentafluoroethyl-N-[2, 4-dinitro-6-(trifluoromethyl)phenyl-1-naphthalenamine 6,7-Dimethyl-4-(1,1,2,2-tetrafluoroethoxy)-N-[2,4-dinitro-6-(trifluoromethyl)phenyl],-1-naphthalenamine 2-Isopropyl-4-chloro-N-[3-chloro-2,4-dinitro6-(trifluoromethyl)phenyl]-1-naphthalenamine 8-n-Butyl-4-(4,4,4-trifluorobutoxy)-N-[3-b-romo2,4-dinitro-6-(trifluoromethyl)phenyl]-1-naphthalenamine 3-Methyl-6-propyl-4-heptafluoropropyl-N-[2,4-dinitro-6-(trifluoromethyl)phenyl]-1-naphthalenamine 3,4-Dichloro-N-[2,4-dinitro-6-(trifluoromethyl)phenyl]-1-naphthalenamine 4-(1,1-Difluoroethoxy)-N-[2,4-dinitro-6-(trifluoromethyl)phenyl]-1-naphthalenamine 4-(1,1,2,2-Tetrafluoroethoxy)-N-2,4-dinitro6-(trifluoromethyl)phenyl]-1-naphthalenamine and 4-(1,1,2,2-Tetrafluoroethylthio)-N-[2,4-dinitro-6-(trifluoromethyl)phenyl ]-1-naphthalenamine.

Anticoccidial combinations comprising nicarbazin or 4,4'-Dinitrocarbanilide and polyether antibiotics are disclosed by Maurice E. Callender and Thomas K. Jeffers in U.S. Pat. No. 4,218,438, issued Aug. 19, 1980. Anticoccidial combinations of the napthalenamines of formula 4 with polyether antibiotics are disclosed by Albert J. Clinton and George O. P. O'Doherty in copending application Ser. No. 374,801, filed May 4, 1982. Anticoccidial combinations comprising the specified benzenamines and a polyether antibiotic are disclosed by Clinton and O'Doherty in U.S. Pat. No. 4,366,168. A coccidiocidal combination of monensin (a polyether antibiotic) and metichlorpindol is disclosed by Larry R. McDougald in U.S. Pat. No. 4,061,755, issued Dec. 6, 1977.

Nicarbazin and 4,4',-dinitrocarbanilide are taught in U.S. Pat. No. 2,731,382. Nicarbazin is a complex of 4,4'-dinitrocarbanilide and 2-hydroxy-4,6-dimethylpyrimidine, but the 4,4'-dinitrocarbanilide alone exhibits anticoccidial activity. See Science 122, 244 (1955).

The components of the combinations of an A80190 compound with compounds 2(a)–(e) are used in amounts which, in combination, are synergistic as to at least one coccidiosis-causing organism. In general, the maximum amounts to be used in the combinations are the same as the maximum amounts for anticoccidial treatment by the individual components. The lower limits are generally less than that required for therapy by the individual components. Accordingly, the present invention is generally practiced with compositions containing (1) from about 2 to about 100 ppm of an A80190 compound and (2) (a) from about 5 to 125 ppm of nicarbazin,(b) from about 25 to about 150 ppm of 4,4'-dinitrocarbanilide, (c) from about 1 to about 1000 ppm of the specified napthalenamine, (d) from about 5 to about 125 ppm of a specified benzenamine, or (e) from about 20 to about 70 ppm of metichlorpindol. The A-80190 compounds are particularly effective when administered with nicarbazin. Preferred combinations contain from about 2 to about 20 ppm of an A80190 compound with from about 5 to about 50 ppm of nicarbazin.

Another important property of the A80190 compounds is the ability to improve feed-utilization efficiency in animals. For example, the A80190 compounds improve feed-utilization efficiency in ruminants which have a developed rumen function.

The efficiency of feed use can be monitored by observing the production and concentration of propionate compounds in the rumen usin described by Arthur P. Raun in U.S. Pat. No. 3,794,732 (see especially Example 5). Table IX shows the ratio of volatile-fattyacid (VFA) concentrations in A80190-treated flasks to concentrations in control flasks in this test.

TABLE IX

Effect of A80190 Compounds on Ruminant Feed-Utilization Efficiency[a]

| Compound[b] | Dosage mcg/ml | Molar % Propionate | Molar % Acetate | Molar % Butyrate | Total VFA/ Control VFA mM/L |
|---|---|---|---|---|---|
| A80190 | 1 | 1.185* | 0.986 | 0.851 | 0.916 |
| A80190 | 1 | 1.403* | 0.892 | 0.813 | 0.887 |
| A80190 | 0.3 | 1.220* | 0.970 | 0.819 | 0.967 |
| AcA80190 | 0.3 | 1.091* | 0.995 | 0.912 | 1.003 |
| PrA80190 | 0.3 | 1.049 | 1.022 | 0.908 | 0.948 |
| A80190 | 1 | 1.247* | 1.016 | 0.706 | 0.857 |
| AcA80190 | 1 | 1.192* | 1.006 | 0.783 | 0.909 |
| PrA80190 | 1 | 1.158* | 1.021 | 0.792 | 0.961 |
| A80190 | 3 | 1.368* | 0.998 | 0.611 | 0.963 |
| AcA80190 | 3 | 1.213* | 1.041* | 0.696 | 1.010 |
| PrA80190 | 3 | 1.195* | 1.033 | 0.731 | 0.930 |
| A80190 | 1 | 1.566* | 0.926 | 0.529 | 0.913 |
| AcA80190 | 1 | 1.196* | 0.976 | 0.833 | 0.777 |
| PrA80190 | 1 | 1.244* | 0.983 | 0.764 | 0.883 |

*LSD; two-tailed t-test; significant at P<0.01; $C_3$ >95 percent upper confidence limit
[a]Three test runs
[b]AcA801190 = acetyl derivative of A80190 PrA80190 = propionyl derivative of A80190

The A80190 compounds are typically effective in increasing propionates and, thereby, the efficiency of feed utilization when administered to ruminants orally at rates of from about 0.02 mg/kg/day to about 1.5 mg/kg/day. Preferable rates of administration are from about 0.05 mg/kg/day to about 0.5 mg/kg/day.

A preferred method of administration is to mix the compound with the animals' feed; however, it can be administered in other ways, for example, tablets, drenches, boluses, or capsules. Formulation of these various dosage forms can be accomplished by methods well known in the veterinary pharmaceutical art. Each individual dosage unit should contain a quantity of a compound of this invention directly related to the proper daily dose for the animal to be treated.

This invention further relates to feed compositions adapted to increase feed utilization comprising feed ration and from 2.5 to 25 grams per ton of an A80190 compound.

As described supra, A80190 compounds are active against anaerobic bacteria, particularly Clostridium perfringens. A80190 compounds are, therefore, beneficial in the treatment or prevention of enteritis in chickens, swine, cattle and sheep. A80190 compounds are also useful in the treatment of enterotoxemia in ruminants.

The A80190 compounds are also anthelmintic agents. For example, A80190 is active against Caenorhabditis elegans at levels as low as 20 ppm.

In another aspect the A80190 compounds are useful in the treatment of swine dysentery. A80190 inhibits the growth of Treponema hyodysenteriae, a causative agent of swine dysentery, at levels as low as 0.39 mcg/ml. A preferred method of administration to swine is by incorporation of an appropriate amount of an A80190 compound into the feed ration or drinking water. An appropriate amount will relate to whether the treatment is to prevent or to cure infection. Usually, a lower concentration of active compound is needed to prevent infection than is required for to eliminate infection in animals already afflicted. In general, amounts in the range of from about 20 to about 100 grams of A80190 compound per ton of feed are effective to prevent infection. Amounts in the range of from about 100 to about 500 g of A80190 compound per ton of feed are recommended for treating swine suffering from dysentery. These amounts provide from about 1 to about 5 mg/kg of body weight per day (prophylactic treatment) or from about 5 to about 25 mg/kg of body weight per day (treatment of infected animal). When added to the drinking water, amounts of from about 0.04 to about 0.2 g (prophylactic) or from about 0.2 to about 1 g (therapeutic) of A80190 compound per gallon of water are recommended.

This invention further relates to feed compositions for treating swine dysentery comprising swine ration and an effective amount of an A80190 compound for this purpose. As discussed, an effective amount is typically one in the range of from about 20 to about 500 grams of A80190 compound per ton of feed.

The A80190 compounds can be administered to animals orally or parenterally. They can also be administered by insufflation, i.e. by blowing the antibiotic, in the form of a medicated dust, into an enclosed space or room wherein the animals or poultry are held. The animals or poultry breathe the medicated dust present in the air; the medicated dust also is taken into the body through the eyes (a process called intraocular injection).

The most practical way to administer the A80190 compounds is by formulation into the feed supply. A variety of feeds, including the common dry feeds, liquid feeds, and pelleted feeds, may be used. Although the preferred method of administration is by mixing it with the animals', feed, it can also be administered in other ways, for example, tablets, drenches, boluses, or capsules. Each individual dosage unit should contain a quantity of A80190 compound directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid of solid preparations.

The final formulation of feeds for animals or poultry will depend upon the amount of drug to be administered. The common methods of formulating, mixing, an pelleting feeds may be used to prepare feeds containing an A80190 compound.

The A80190 compounds may be formulated for parenteral administration by methods recognized in the veterinary pharmaceutical art. Effective injectable compositions containing the A80190 compounds may be in either suspension or solution form. In the solution form, the A80190 compound is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the liquid nonsolvent can assist in making injectable suspensions in individual cases. For example, silicone antifoams, glycols, sorbitol, and sugars can be useful suspending agents.

In the preparation of dusts or powders for administration by insufflation, the compounds are typically mixed with talc, diatomaceous earth, or some other inert substance as an adjuvant.

The A80190 compounds are also useful as insecticides and acaricides. For example, A80190 is active against the following insects as levels as low as the level indicated in parenthesis: mosquito larvae ($<50$ ppm), blowfly larvae (35 ppm), adult housefly (35 ppm), and Mexican bean beetle and southern armyworm ($<100$ ppm). A80190 is also active against mites such as two-spotted spider mite when applied at a rate as low as 25 ppm.

In another aspect, the A80190 compounds have herbicidal activity. For example, A80190 is active against crabgrass, mustard and pigweed at 2 lb/acre (200 gpa) either pre-emergence or post-emergence.

The A80190 compounds are active against polio virus. For example, tissue-culture tests show that A80190 is active against Polio III virus at a level of 2000 $\mu$g/ml.

Antibiotic A80190 exhibits ion-transport properties and is, therefore, an ionophore (ion-bearer) (see B. C. Pressman, Alkali metal chelators the ionophores, in "Inorganic Biochemistry," Volume 1, G. L. Eichhorn, Elsevier, 1973). At a 0.5 $\mu$g/ml concentration A80190 showed ionophorous activity; its activity with $Na^+$, $K^+$ and $Rb^+$ was better than that with $Cs^+$ or $Li^+$. At a lower contentration (0.2$\mu$g/ml), however, A80190 exhibited an even greater ionophorous effect with $Cs^+$ than with $Na^+$ as cation.

A80190 can be used, therefore, when the selective removal of particular cations is desired. Examples of such uses include the removal and recovery of silver ions from solutions in photography, the removal of toxic cations from industrial waste streams before such streams are discharged to the environment, and desalinization of sea water. A80190 can be used as one component of an ion-specific electrode (see O. Kedem, et al., U.S. Pat. No. 3,753,887, Aug. 21, 1973).

A80190 alters the cation permeability of both natural and artificial membranes. A80190 can be used, therefore, as a component in a membrane used for the selective transport of cations against a concentration gradient. One potential application of this property is in recovery of heavy and precious metals on a commercial basis [see E. L. Cussler, D. F. Evans, and Sister M. A. Matesick, Science 172, 377 (1971)].

In yet another aspect, the A80190 compounds are active as inhibitors of the enzyme ATPase. ATPase, an alkali-metal-sensitive enzyme found in cell membranes, is involved in the energy necessary for active transport. "Active transport" refers to the energy requiring series of operations whereby intracellular and extracellular fluids maintain their compositions. Inhibitors of ATPase reduce the energy required for active transport. In vitro tests have shown that A80190 inhibits mitochondrial ATPase with a half-effective concentration ($IC_{50}$) of 0.5 $\mu$g/ml.

The A80190 compounds are also potential cardiotonic agents.

In order to illustrate more fully the operation of this invention, the following examples are provided:

EXAMPLE 1

Preparation of A80190

A. Shake-flask Fermentation of A80190

The culture *Actinomadura oligospora* NRRL 15878, either as a lyophilized pellet or as a suspension maintained in liquid nitrogen, is used to inoculate a seed medium having the following composition:

| SEED MEDIUM | |
|---|---|
| Ingredient | Amount (%) |
| Glucose | 1.0 |
| Soluble starch | 2.0 |
| Yeast extract | 0.5 |
| Enzymatic hydrolysate of casein* | 0.5 |
| CaCO$_3$ | 0.1 |
| Deionized water | q.s. 1 liter |

*NZ Amine A, Sheffield Chemical Co., Norwich, N.Y.

NaOH was added to raise the pH of the medium to about 7.2 before sterilizing.

Slants or plates are prepared by adding 2.5% agar to the seed medium. The inoculated slant is incubated at 30° C. for from about 10 to about 14 days. The mature slant culture is scraped with a sterile tool to loosen the spores and remove and mascerate the mycelial mat. About one-fourth of the loosened spores and culture growth thus obtained is used to inoculate 50 ml of a first-stage seed medium.

The inoculated first-stage medium is incubated in a 250-ml Erlenmeyer flask at 30° C. for about 48 hours on a shaker orbiting in a two-inch (5.08 cm) circle at 250 rpm.

This incubated first-stage medium (0.4 ml) is used to inoculate 50 ml of a production medium having the following composition:

| Ingredient | Amount (%) |
|---|---|
| Glucose | 3.0 |
| N—Z Amine A | 0.4 |
| Collagen hydrolysate* | 0.5 |
| MgSO$_4$.7H$_2$O | 0.05 |
| CaCO$_3$ | 0.2 |
| Cold tap water | q.s. 1 liter |

*IPC 3, Inland Industrial Molasses Co., Dubuque, Iowa (Presterilization pH adjusted to 7.0)

The inoculated production medium is incubated in a 250-ml wide-mouth Erlenmeyer flask at 30°-32° C. for 8 to 10 days on a shaker orbiting in a two-inch circle at 250 rpm.

B. Tank Fermentation of A80190

In order to provide a larger volume of inoculum, 10 ml of incubated first-stage medium, prepared as described in Section A, is used to inoculate 400 ml of a second-stage growth medium having the same composition as that of the first-stage medium. This second-stage vegetative medium is incubated in a two-liter wide-mouth Erlenmeyer flask for about 48 hours at 30° C. on a shaker orbiting in a two-inch circle at 250 rpm.

Incubated second-stage vegetative medium (800 ml) thus prepared is used to inoculate 100 liters of sterile production medium, prepared as described in Section A. The inoculated production medium is allowed to ferment in a 165-liter stirred fermentation tank for 8 to 10 days at a temperature of 30°-32° C. Low airflow (0.12-0.25 v/v/m) and low rpm (150-200) in the stirred vessel maintain a dissolved oxygen level above 30% of air saturation.

EXAMPLE 2

Isolation of A80190

Whole fermentation broths from two 100-L tanks were combined (207 L) and filtered through a filter press with the aid of Hyflo Supercel. The mycelial filter cake was extracted by circulating methanol (40 L) through the filter press. Acetone can also be used as an extractant. The methanol extract, concentrated in vacuo to a volume of about 15 L, was combined with the broth filtrate (182 L). This was adjusted to pH 9 with 1N sodium hydroxide, and the resulting solution was extracted with an equal volume of ethyl acetate. The ethyl acetate extract was concentrated to a volume of about 700 ml. Water (1 L) was added to the concentrated extract; the pH was adjusted to 9.0 with sodium hydroxide; and the mixture was extracted twice with toluene (1 L), maintaining the pH at 9.0. The toluene extracts were combined and concentrated in vacuo to give an oily residue containing A80190.

The residue was dissolved in toluene (100 ml) and applied to a column containing 2 L of silica gel (Woelm, 70-150 mesh) in toluene. The column was eluted first with toluene (10 L) and then with toluene:ethanol mixtures (49:1, 10 L) and (48:2, 10 L), collecting 1-L fractions. Elution was monitored by bioassay and TLC. Fractions containing A80190 were combined and concentrated. The residue was dissolved in dioxane and freeze-dried to yield 13.6 g of crude A80190.

EXAMPLE 3

Purification of A80190

Crude A80190 (20.4 g), obtained from four 100-L tanks as described in Examples 1 and 2, was dissolved in acetonitrile (200 ml). The solution was applied to a column containing 2 L of silica gel (Woelm, 70-150 mesh) in acetonitrile. The column was washed with acetonitrile (10 L) and eluted sequentially with acetonitrile:acetone mixtures (95:5, 2 L), (9:1, 10 L), (4:1, 10 L) and (7:3, 10 L), collecting 1-L fractions. Elution was monitored by bioassay, using *Bacillus subtilis*. Fractions containing A80190 were combined and concentrated. The residue was dissolved in dioxane and freeze-dried to yield 15.8 g of purified A80190.

EXAMPLE 4

Crystallization of A80190

Purified A80190 (28.2 g), was dissolved in acetone (500 ml). Water (500 ml) was added, and the pH was adjusted to 5.0 with dilute hydrochloric acid. The resulting solution was allowed to stand at room temperature for 20 hours for crystallization to occur. The crystals were separated by filtration, washed with water and dried in a vacuum oven to yield 25.9 g of crystalline A80190 (acid form).

EXAMPLE 5

Preparation of A80190 Sodium Salt

Figure 2:
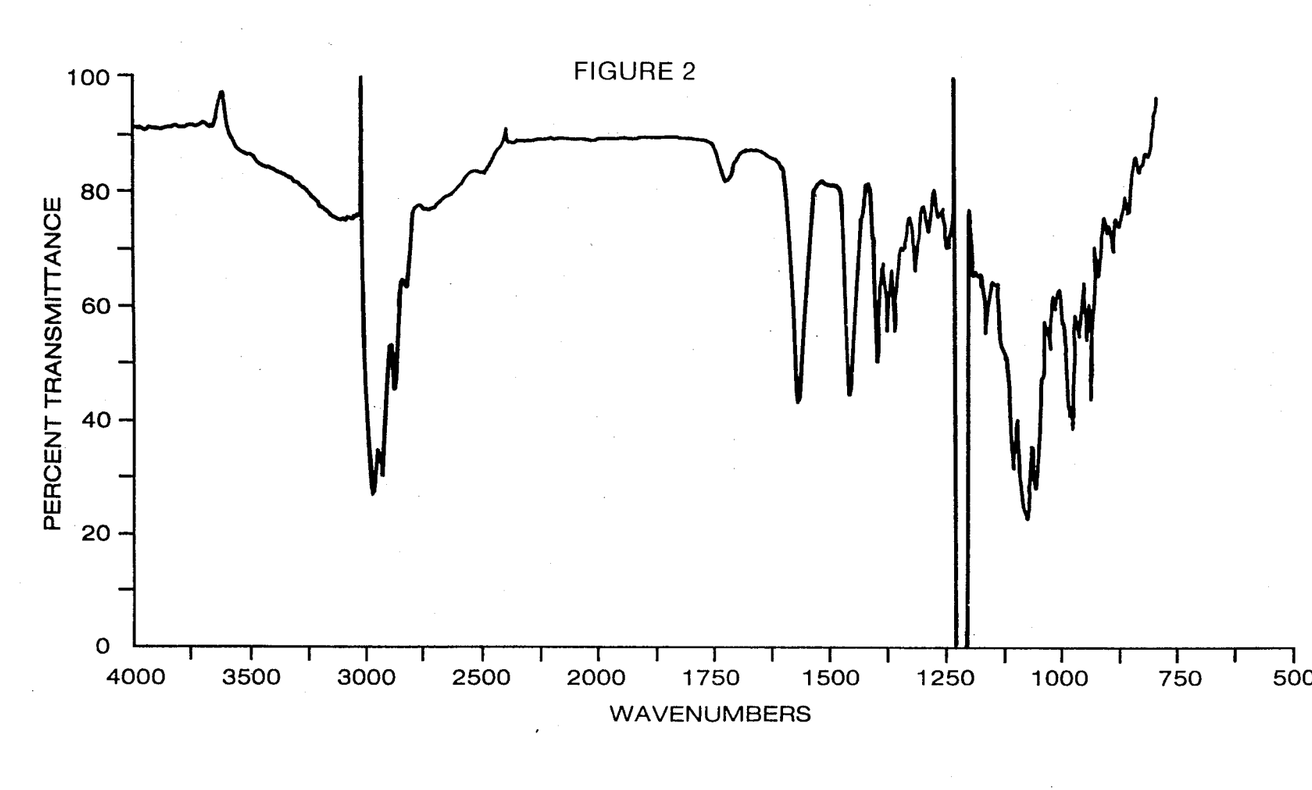
FIG. 2 shows the infrared absorption spectrum of A80190 sodium salt in chloroform.

A80190 (acid form, 300 mg) was dissolved in acetone (30 ml); water (10 ml) was added; and the pH was adjusted to 10 with NaOH. The solution was concentrated to an oily residue which was dissolved in dioxane and freeze-dried to yield a white powder (m.p. 145°-150°). The molecular weight of the product by field desorption mass spectrometry (FDMS) was 850. IR in CHCl$_3$, shown in FIG. 2, shows absorption maxima at the following frequencies (cm$^{-1}$): 2962, 2934, 2885, 2825, 1719, 1569, 1455, 1397, 1377, 1358, 1314, 1285, 1243, 1162, 1104, 1074, 1057, 1025, 987, 979, 936, 922, 895 and 847.

EXAMPLE 6

Alternate Preparation of A80190 Sodium Salt

A80910 (acid form, 5 g) was dissolved in ethyl acetate (500 mg); water (500 ml) was added. The mixture was adjusted to pH 10 with 5N NaOH, stirring for 15 minutes to maintain the pH. The ethyl acetate phase was separated and washed with water (500 ml) and concentrated under vacuum to dryness. The residue was dissolved in dioxane (100 ml) and freeze-dried to give 4.1 g of the sodium salt of A80190.

The water wash was allowed to stand at room temperature overnight, and the crystals which formed were filtered and dried. The crystals were A80190 in the acid form (mp 115°-120° C.).

EXAMPLE 7

Crystallization of A80190 Sodium Salt

A80190 sodium salt (1 g) was dissolved in pentane (10 ml) and allowed to stand at room temperature for three days (solvent evaporates to about 5 ml). The crystals which formed were filtered and dried under vacuum to give 593 mg of crystalline A80190 sodium salt, mp 225°-230° C.

EXAMPLE 8

Preparation of Acetyl A80190

Figure 3:
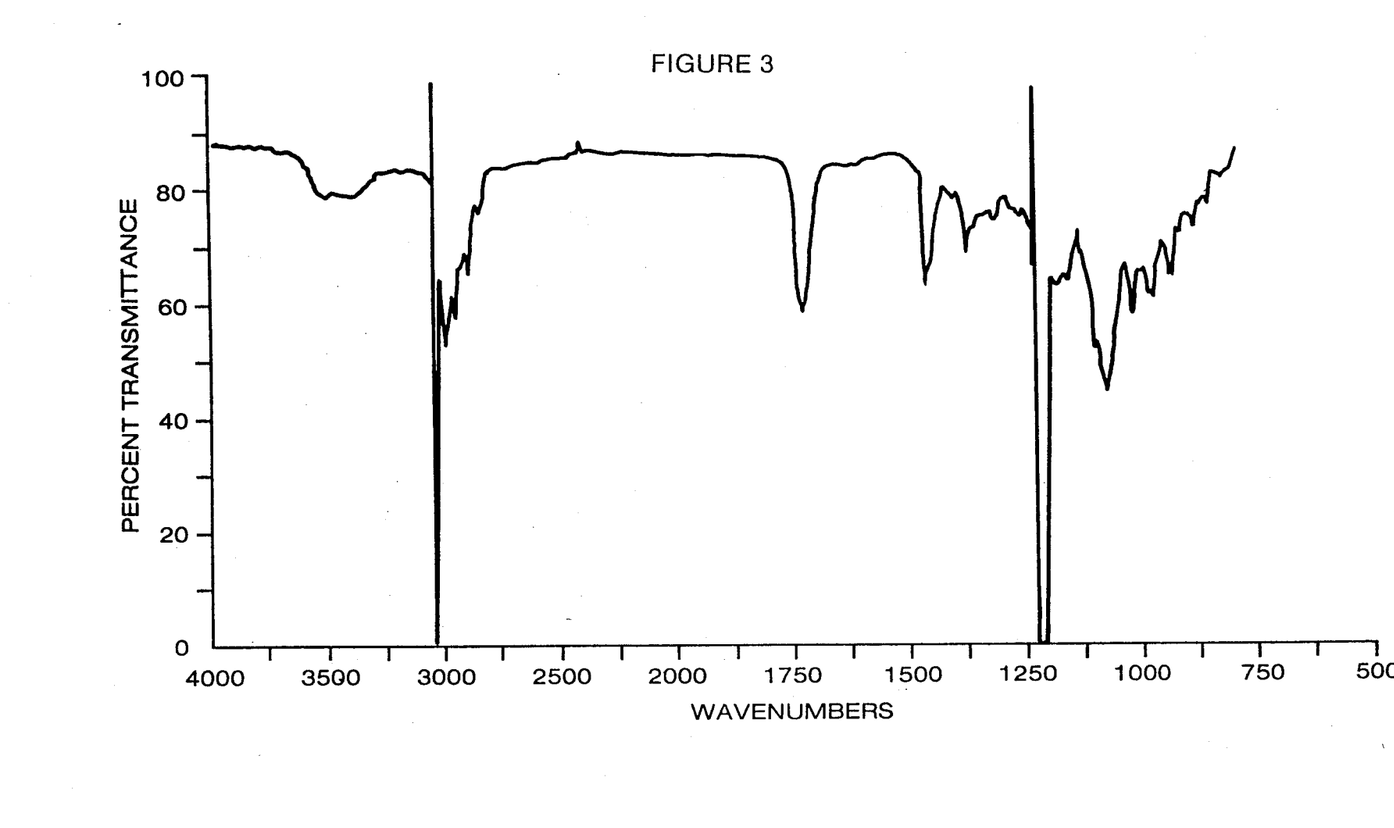
FIG. 3 shows the IR spectrum of A80190 acetyl ester derivative in chloroform.

A80190 (acid form, 200 mg) was dissolved in pyridine (4 ml); acetic anhydride (4 ml) was added; and the mixture was allowed to stand for 72 hours at room temperature. Water (10 ml) was added, and the aqueous solution was extracted with chloroform (50 ml). The chloroform extract was washed successively with 50 ml each of 0.1N HCl, water containing 1 percent NaHCO$_3$, and water. The chloroform extract was then concentrated in vacuo to a residue, and the residue was dissolved in acetone (100 ml). The acetone solution was concentrated in vacuo to remove residual pyridine and acetic acid. This step was repeated three times, and the resulting residue was dissolved in acetone (50 ml). Water (50 ml) was added, and the resulting solution was allowed to stand at room temperature for crystallization to occur. The crystals were separated by filtration, washed with water and dried in a vacuum oven at 50° C. to yield 192 mg of crystalline acetyl A80190 (m.p. 87°-89° C.). Molecular weight=870 by fast-atom bombardment mass spectrometry (FABMS). IR in CHCl$_3$, shown in FIG. 3, shows absorption maxima at the following frequencies (cm$^{-1}$): 3021, 3018, 2935, 2825, 1726, 1454, 1373, 1311, 1244, 1162, 1104, 1078, 1058, 1024, 987, 976, 934 and 925.

EXAMPLE 9

Preparation of Propionyl A80190

Figure 4:
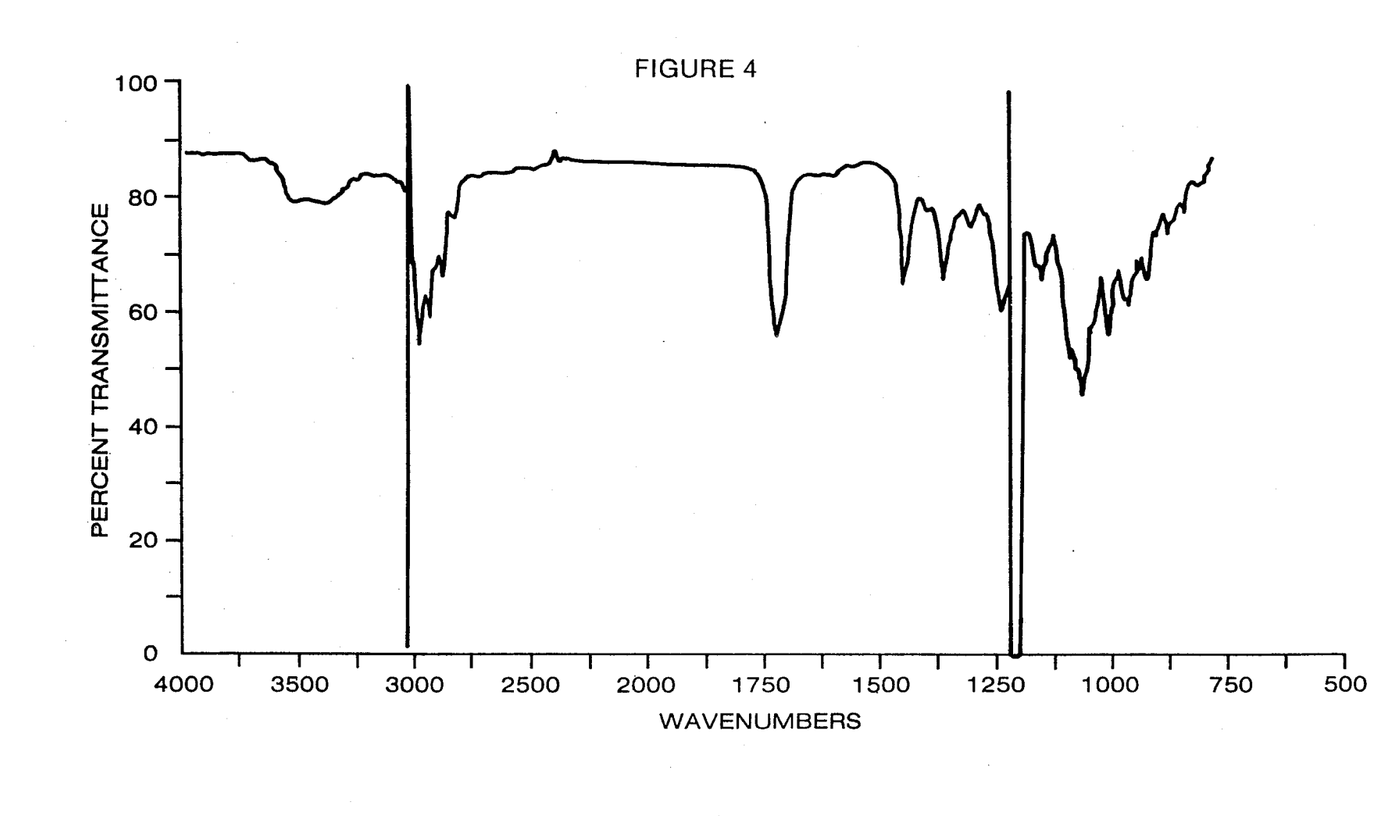
FIG. 4 shows the IR spectrum of A80190 propionyl ester derivative in chloroform.

A80190 (acid form, 200 mg) was dissolved in pyridine (4 ml); propionic anhydride (4 ml) was added; and the mixture was allowed to stand at room temperature for 72 hours. Water (10 ml) was added, and the solution was extracted with chloroform (50 ml). The chloroform extract was washed successively with 50 ml each of 0.1N HCl, water containing 1 percent NaHCO$_3$ and water. The chloroform extract was concentrated in vacuo to a residue which was dissolved in acetone (100 ml). The acetone solution was concentrated in vacuo to remove residual pyridine and acetic acid. This step was repeated three times. The residue was dissolved in acetone (50 ml); water (50 ml) was added; and the mixture was allowed to stand at room temperature for 16-20 hours for crystallization to occur. The crystals were separated by filtration, washed with water and dried in a vacuum oven at 50° C. to yield 170 mg of crystalline propionyl A80190 (m.p. 83°-85° C.). Molecular weight of 884 by FDMS and FABMS. IR in CHCl$_3$, shown in FIG. 4, shows absorption maxima at the following frequencies (cm$^{-1}$): 3018, 2976, 2935, 2827, 1725, 1460, 1376, 1313, 1160, 1105, 1082, 1058, 1024, 987, 979, 945, 935 and 893.

EXAMPLES 10-12

The following A80190 ester derivatives can be prepared using the method of Examples 8-9:
n-Heptanoyl A80190
Valeryl A80190
tert-Butyryl A80190

EXAMPLE 13

Preparation of A80190 4-Bromophenylurethane Derivative

A80190 (acid form, 7 g) was dissolved in benzene (100 ml), and 4-bromophenyl isocyanate (3 g) in benzene (100 ml) was added with stirring. The mixture was stirred at room temperature for 168 hours. The reaction was monitored daily by silica-gel TLC, using acetonitrile:acetone (1:1) as the developing solvent and detecting with vanillin-H$_2$SO$_4$ spray reagent. The reaction appeared to be complete by 168 hours. The precipitate which formed was separated by filtration, and the filtrate containing the derivative and some unreacted A80190 was concentrated and lyophilized to give 7.5 g of product.

This product was dissolved in acetonitrile (50 ml) and applied to a 3- ×140-cm column containing 800 ml of silica gel (Woelm, 70-150 mesh) in acetonitrile. The column was developed with acetonitrile, collecting a first fraction having a volume of 500 ml, five subsequent fractions of 100 ml each and then six fractions of 500 ml each. Elution was monitored by silica-gel TLC. Crystals formed in the fourth fraction after standing at room temperature overnight. The crystals were separated by filtration and dried under vacuum to give 689 mg of A80190 4-bromophenylurethane derivative.

The filtrate was dried. The residue was dissolved in dioxane (50 ml) and lyophilized to give an additional 477 mg of the product. The fifth through the tenth fractions were combined and concentrated to dryness. The residue was dissolved in acetonitrile (50 ml) and lyophilized to give an additional 2.3 g of amorphous A80190 4-bromophenyl urethane derivative. This compound had the following characteristics:
mp: 142°-145° C.
$[\alpha]_D^{25}$: +4° (c 10, CHCl$_3$)
molecular weight: 1025 (fast-atom-bombardment mass spectrometry)

EXAMPLES 14-15

The following A80190 urethane derivatives were prepared using the method of Example 13: A80190 4-chlorophenylurethane derivative and A80190 4-nitrophenylurethane derivative.

EXAMPLES 16-23

The following urethane derivatives can be prepared used the method of Example 13:
A80190 phenylurethane
A80190 4-methylphenylurethane
A80190 4-iodophenylurethane
A80190 4-fluorophenylurethane
A80190 cyclohexylurethane
A80190 2-phenethylurethane
A80190 2-(phenyl)cyclopropylurethane
A80190 4-phenoxyphenylurethane

EXAMPLE 24

Preparation of A80190 Methyl Ether Derivative

A80190 in the acid form is dissolved in methanol; water (½ volume) is added. The solution is allowed to stand until the ether derivative is formed. The solution is evaporated under vacuum. The product is chromatographed using, for example, silica gel to give to A80190 methyl ether derivative.

EXAMPLES 25 to 27

Using a procedure like that of Example 24 and the appropriate alcohol or thiol, the following A80190 ether derivatives can be prepared:
A80190 n-Propyl Ether Derivative
A80190 Methyl Thioether Derivative
A80190 n-Butyl Ether Derivative Chromatographic Identification of A80190

EXAMPLE 28

| I. TLC on silica gel | |
| --- | --- |
| System: | acetonitrile:acetone (1:1) |
| $R_f$ = 0.59 | |
| Detection: | *Bacillus subtilis* |
| | Vanillin-$H_2SO_4$ spray |
| II. HPLC | |
| Adsorbent: | μBondapak C18 (4 × 300-mm column) |
| Solvent system: | acetonitrile:tetrahydrofuran:$H_2O$ (6:1:3) containing 1 percent $H_3PO_4$; adjusted to pH 3.0 with $NH_4OH$ |
| Detection: | refractometer |
| Flow rate: | 3.0 ml/min |
| Retention time: | 9.7 min |

EXAMPLE 29

A80190 is prepared by the method of Example 1, but using the *Actinomadura oligospora* NRRL 15877 culture.

EXAMPLE 30

A80190 Modified Chick Ration for Coccidiosis Control

A balanced, high-energy ration adapted to feed chicks for rapid weight gain is prepared by the following recipe:

| Ingredient | % | lbs |
| --- | --- | --- |
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and $B_{12}$, choline, niacin, pantothenic acid, riboflavin, biotin, with glucose bulking agent) | 0.5 | 10 |
| Trace mineral premix (representing $MnSO_4$, ZnO, KI, $FeSO_4$, $CaCO_3$) | 0.2 | 4 |
| 2-Amino-4-hydroxybutyric acid (hydroxy analog of methionine) | 0.1 | 2 |
| A80190 (Na Salt) | 0.01 | 0.2 |

These substances are mixed in accordance with stand feed-mixing techniques. Chicks fed such a ration, with water ad libitum, are protected against exposure to coccidiosis; weight gains are comparable to those of coccidiosis-free chicks fed a similar, unmedicated diet.

EXAMPLE 31

A80190-Improved Beef-Cattle Ration

A balanced high-grain beef-cattle ration is prepared as follows:

| Ingredient | % | lbs |
| --- | --- | --- |
| Finely ground corn | 67.8 | 1356 |
| Ground corn cob | 10 | 200 |
| Dehydrated alfalfa meal, 17 percent protein | 5 | 100 |
| Dehulled soybean meal, solvent extracted, 50 percent protein | 9.9956 | 199.912 |
| Cane molasses | 5 | 100.0 |
| Urea | 0.6 | 12.0 |
| A80190 (Na salt) | 0.0044 | 0.088 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and $D_2$ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin $D_2$ and 385.7 g of soybean feed with 1% oil added
**Corn distillers dried grains with solubles containing 20,000 I.U. of d-alpha-tocopheryl acetate per pound The mixed feed is compressed into pellets. At an average daily ingestion rate of 15 pounds of feed per animal, this feed supplies approximately 300 mg of A80190 (Na salt) per animal per day.

EXAMPLE 32

A80190-Improved Swine Ration

A balanced swine farrowing ration is prepared as follows:

| Ingredient | % | lbs/ton |
|---|---|---|
| Ground yellow corn | 65.10 | 1302 |
| Soybean oil meal, solvent extracted dehulled | 18.50 | 370 |
| Dried-beet pulp | 10.00 | 200 |
| Dicalcium phosphate | 2.90 | 58 |
| Calcium carbonate | 1.20 | 24 |
| Swine vitamine premix[1] | 1.10 | 22 |
| Salt (NaCl) | 0.55 | 11 |
| Choline chloride, 25% | 0.35 | 7 |
| Trace-mineral premix[2] | 0.15 | 3 |
| Vitamin A premix[3] | 0.10 | 2 |
| Hydroxy analog of Methionine | 0.05 | 1 |
| Total | 100.00 | 2000 |

[1] Each kg of premix contains the following: 77,161 USP units Vitamin $D_2$; 2,205 I.U. of Vitamin E; 441 mg riboflavin; 1,620 mg pantothenic acid; 2,205 mg niacin; 4.4 mg Vitamin $B_{12}$; 441 mg Vitamin K; 19,180 mg choline; 110 mg folic acid; 165 mg pyridoxine; 110 mg thiamine; 22 mg biotin.
[2] Each kg of premix contains the following: 50 g of manganese as manganese sulfate; 100 g of zinc as zinc carbonate; 50 g of iron as ferrous sulfate; 5 g of copper as copper oxide; 1.5 g of iodine as potassium iodide and 150 g maximum and 130 g minimum calcium as calcium carbonate.
[3] Each kg of premix contains 6,6138,00 USP units Vitamin A.

For 200 pounds of this ration, a premix is prepared by adding A80190 (10 g) to a small amount of solvent-extracted soybean feed, grinding them in a mortar and pestle, and diluting the ground mixture to one pound with additional solvent-extracted soybean feed. This premix is then added to 200 lb. of the above-described swine ration, mixing by standard techniques. This medicated feed provides a level of 100 grams of A80190 per ton of basal ration. Medicated feed is fed to sows for at least one day, and preferably from seven to ten days, prior to farrowing and after farrowing for as long as is desirable.

Larger or smaller quantities of medicated ration with varying levels of A80190 are prepared by varying the quantity of A80190 in the premix and/or the quantity of basal ration.

Sows are fed at rates of from 1.0 to 10 grams of A80190 per 100 pounds of feed. The medicated feed is available ad libitum with water. Usually, sows consume about 6–8 lb of ration per day.

EXAMPLE 33

A80190-Formulation for Piglets

A80190 is dissolved in a small amount of ethanol. This ethanol solution is suspended in polyethylene glycol 200. The suspension is concentrated so that each unit dose has a volume of about 0.5 to 2 ml. Such suspensions are given to young pigs at rates of 0.5 to 50 mg per lb, three times a day by gavage.

EXAMPLE 34

Improved Ration for Control of Swine Dysentery

A premix is prepared by standard methods using the following ingredients:

| Ingredient | Grams/Kilogram |
|---|---|
| Active Compound | 150.0 |
| Calcium Silicate | 20.0 |
| Calcium Carbonate (Oyster Shell Flour) | 830.0 |
| Total Weight | 1000 gms. |

This premix is added to commercial swine ration, using standard feed-mixing techniques, to give a final level of active compound of 100 grams/ton.

We claim:

1. A process for producing antibiotic A80190 which comprises cultivating *Actinomadura oligospora* NRRL 15877, or an A80190-producing mutant thereof, in a culture medium containing assimilable sources of carbon, nitrogen, and inorganic salts under submerged aerobic fermentation conditions until a recoverable amount of antibiotic A80190 is produced.

2. The process of claim 1 which includes the additional step of separating A80190 from the culture medium.

3. The process of claim 1 wherein *A. oligospora* NRRL 15877 is used.

4. A biologically purified culture of the microorganism *Actinomadura oligospora* NRRL or an A80190-producing mutant thereof.

5. The culture of claim 4 which is *Actinomadura oligospora* 15877.

* * * * *

UNITED STATES PATENT AND TRADEMARK OFFICE
CERTIFICATE OF CORRECTION

PATENT NO. : 4,683,201
DATED : July 28, 1987
INVENTOR(S) : Robert L. Hamill and Raymond C. Yao It is certified that error appears in the above-identified patent and that said Letters Patent is hereby corrected as shown below:

Column 28, line 41:   "NRRL or"

should read -- NRRL 15877 or --.

Signed and Sealed this

Eighth Day of August, 1989

Attest:

DONALD J. QUIGG

Attesting Officer

Commissioner of Patents and Trademarks